(12) United States Patent
Infeld et al.

(10) Patent No.: US 7,014,866 B2
(45) Date of Patent: Mar. 21, 2006

(54) HIGH DOSE SOLID UNIT ORAL PHARMACEUTICAL DOSAGE FORM OF AMORPHOUS NELFINAVIR MESYLATE AND PROCESS FOR MAKING SAME

(75) Inventors: Martin Howard Infeld, Upper Montclair, NJ (US); Wantanee Phuapradit, Clifton, NJ (US); Navnit Hargovindas Shah, Clifton, NJ (US); Lin Zhang, Piscataway, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 261 days.

(21) Appl. No.: 10/138,071

(22) Filed: May 2, 2002

(65) Prior Publication Data

US 2003/0021840 A1    Jan. 30, 2003

Related U.S. Application Data

(60) Provisional application No. 60/288,410, filed on May 3, 2001.

(51) Int. Cl.
*A61K 9/20* (2006.01)
(52) U.S. Cl. ............ 424/464; 424/451; 424/470; 514/772; 514/772.3
(58) Field of Classification Search ............... 424/464, 424/451, 470; 514/772, 772.3
See application file for complete search history.

(56) References Cited

U.S. PATENT DOCUMENTS

| 5,281,420 A | 1/1994 | Kelm et al. |
| 5,834,472 A | 11/1998 | Sangekar et al. |
| 6,001,851 A | 12/1999 | Albizati et al. |
| 6,045,829 A | 4/2000 | Liversidge et al. |
| 6,458,818 B1 * | 10/2002 | Lipari et al. ................ 514/365 |
| 6,692,767 B1 * | 2/2004 | Burnside et al. ............ 424/489 |
| 2001/0018070 A1 | 8/2001 | Shell et al. |

FOREIGN PATENT DOCUMENTS

| WO | WO97/02017 | * 1/1997 |
| WO | WO 98/57648 | 12/1998 |
| WO | WO 01/34118 | 5/2001 |
| WO | WO 01/89679 | 11/2001 |

OTHER PUBLICATIONS

Zhang, K.E., et al., Antimicrobial Agents and Chemotherapy, vol. 45, No. 4, pp. 1086-1093 (2001).
Kaldor et al., "*Viracept (Nelfinavir Mesylate, AG1343)*: A Potent, Orally Bioavailable Inhibitor of HIV-1 Protease" J.Med. Chem. vol. 40, pp. 3979-3985 (1997).
Bardsley-Elliot et al., "*Nelfinavir: An Update on its Use in HIV Infection*", Drugs, vol. 59(3), pp. 581-620 (2000.

* cited by examiner

*Primary Examiner*—Thurman K. Page
*Assistant Examiner*—Lakshmi Channavajjala
(74) *Attorney, Agent, or Firm*—George W. Johnston; Dennis P. Tramaloni; Samuel H. Megerditchian

(57) ABSTRACT

A solid unit oral pharmaceutical dosage form of amorphous nelfinavir mesylate is provided comprising amorphous nelfinavir mesylate in an amount of from about 400 mg to about 700 mg calculated as nelfinavir base, and a pharmaceutically acceptable water soluble, non-ionic synthetic block copolymer of ethylene oxide and propylene oxide, the copolymer having a melting point of at least about 45° C. and an HLB value at 25° C. of from about 18 to about 29, wherein the copolymer is present from about 40% to about 65% by weight of the nelfinavir mesylate. A hot melt granulation process for making the dosage form is provided.

29 Claims, 4 Drawing Sheets

○ Example I
□ Example IV

HIGH DOSE SOLID UNIT ORAL PHARMACEUTICAL DOSAGE FORM OF AMORPHOUS NELFINAVIR MESYLATE AND PROCESS FOR MAKING SAME

BACKGROUND OF THE INVENTION

Nelfinavir mesylate is one of several protease inhibitors used to limit viral replication and improve immune function in HIV-infected individuals. Information regarding nelfinavir mesylate is reported in "Viracept (Nelfinavir Mesylate, AG1343): A Potent, Orally Bioavailable Inhibitor of HIV-1 Protease", Kaldor et al., J. Med. Chem., 40, 3979–85 (1997), and its use in the treatment of HIV is reported in "Nelfinavir: An Update on its Use in HIV Infection", Bardsley-Elliot et al., Drugs, 59(3), 581–620 (2000).

Nelfinavir mesylate is a white to off-white amorphous powder that is slightly soluble in water at pH less than or equal to 4. Nelfinavir mesylate has a molecular weight of 663.90 (567.79 as the free base).

Nelfinavir mesylate is commercially available as a 250 mg tablet (as nelfinavir free base). It is sold under the name Viracept® by Agouron Pharmaceuticals, Inc., a Pfizer company. Viracept® tablets are known to additionally contain calcium silicate, crospovidone, magnesium stearate, FD&C blue #2 powder, hydroxypropyl methylcellulose and triacetin. U.S. Pat. No. 6,001,851 to Albizati et al., assigned to Agouron Pharmaceuticals, Inc., reports a tablet composition (formulation 9) containing 292 mg of an HIV inhibitor which can be nelfinavir mesylate. The patent does not specify the market formulation, Viracept®, although the reported composition contains calcium silicate, crospovidone and magnesium stearate. Calcium silicate and crospovidone each constitute about 25% of the composition reported in the patent.

For adult patients, the recommended oral dosage of nelfinavir mesylate (calculated as nelfinavir free base) is 750 mg (3×250 mg tablets) 3 times daily or an alternative regimen of 1250 mg (5×250 mg tablets) twice daily. Whether a two- or three-times per day dosage program is followed, the tablet burden remains significant over the course of a day. Patient compliance is therefore a real concern.

Block copolymers of ethylene oxide and propylene oxide that are listed as poloxamers in the NF Monograph "Poloxamer" are available in a wide range of molecular weights and melting points. They are marketed under the name Lutrol® or Pluronic® by BASF Corporation. Poloxamers have been extensively used as pharmaceutical wetting and solubilizing agents, typically in small amounts.

It has also been noted that poloxamers can be used in pharmaceutical formulations to enhance the bioavailability of a drug. U.S. Pat. No. 5,834,472 to Sangekar et al., for example, reports that including a non-ionic surfactant that is a block copolymer of ethylene oxide and propylene oxide in a composition of an antifungal compound having extremely low water solubility can enhance the bioavailability of the compound. U.S. Pat. No. 5,281,420 to Kelm et al. addresses formulation of the drug tebufelone, an anti-inflammatory, analgesic and/or antipyretic agent that is essentially water-insoluble. Absorption of tebufelone is quite low from the gastrointestinal tract. Kelm et al. report a solid dispersion of tebufelone, produced by melting together poloxamer and tebufelone (melting point of about 70° C.) to form a homogeneous melt mixture. Solid dispersions of the homogeneous melt mixture result from cooling the mixture and allowing it to solidify. The poloxamer surfactant is included to provide the necessary solubilization of the highly insoluble drug in forming the melt mixture.

A high dosage strength solid unit oral dosage form, e.g., a tablet, of nelfinavir mesylate having satisfactory dissolution and bioavailability has apparently not been successfully developed prior to the present invention. This may be due in part to the hydrophobic nature of the drug, which accounts for its low aqueous solubility. In addition, nelfinavir mesylate in high dose solid unit dosage forms gels upon exposure to physiological fluid. The gel retards dissolution and bioavailability of the drug. The problem of gelling worsens with increased drug loading.

SUMMARY OF THE INVENTION

The present invention provides a solid unit oral pharmaceutical dosage form of amorphous nelfinavir mesylate comprising amorphous nelfinavir mesylate in an amount of from about 400 mg to about 700 mg calculated as nelfinavir base, and a pharmaceutically acceptable water soluble, non-ionic synthetic block copolymer of ethylene oxide and propylene oxide, the copolymer having a melting point of at least about 45° C. and an HLB value at +25° C. of from about 18 to about 29, wherein the copolymer is present from about 40% to about 65% by weight of the nelfinavir mesylate. The high dose nelfinavir mesylate pharmaceutical dosage form of the invention exhibits satisfactory dissolution and bioavailability.

The present invention also provides a process for preparing a solid unit oral pharmaceutical dosage form of amorphous nelfinavir mesylate, comprising: (a) heating a blend of amorphous nelfinavir mesylate in an amount of from about 400 mg to about 700 mg calculated as nelfinavir base per unit dosage and a pharmaceutically acceptable water soluble, non-ionic synthetic block copolymer of ethylene oxide and propylene oxide, the copolymer having a melting point of at least about 45° C. and an HLB value at 25° C. of from about 18 to about 29, in an amount of copolymer that is from about 40% to about 65% by weight of nelfinavir mesylate, at a temperature of from the melting point temperature of the copolymer to below the decomposition temperature of nelfinavir mesylate, (b) mixing the blend to form a melt granulation, and (c) processing the melt granulation into the solid unit oral dosage form of amorphous nelfinavir mesylate.

DETAILED DESCRIPTION OF THE INVENTION

Figure 1:
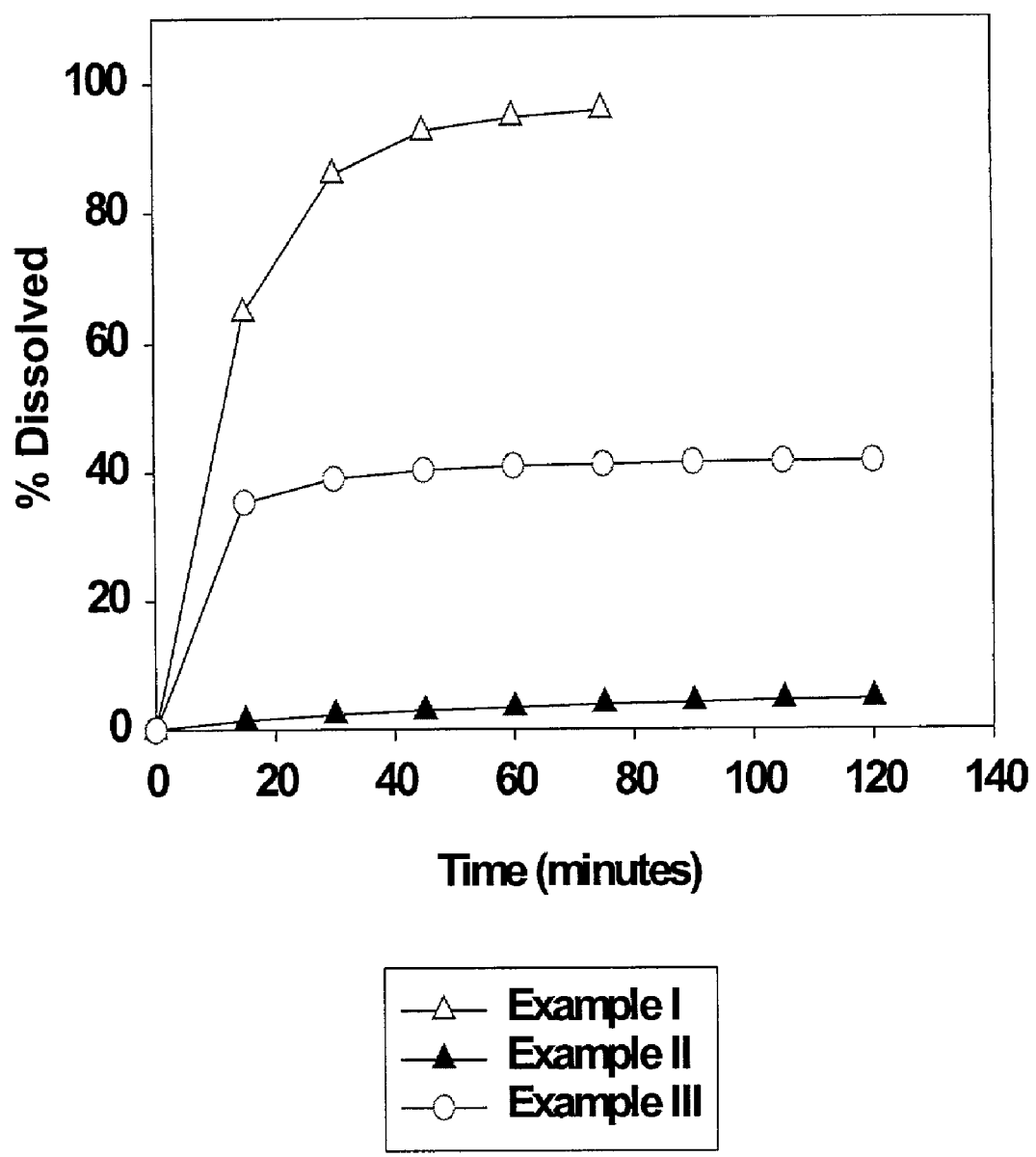
FIG. 1 presents dissolution profiles of 625 mg tablets of nelfinavir mesylate (Examples II and III) compared to that of the 250 mg market (tablet) formulation (Example I).

It has surprisingly been found that when amorphous nelfinavir mesylate is melt granulated with a water-soluble, non-ionic synthetic block copolymer of ethylene oxide and propylene oxide in accordance with the invention, a significant improvement in the dissolution rate of the drug is shown with resulting satisfactory bioavailability. The nelfinavir mesylate of the invention is amorphous. Dosage amounts are calculated as nelfinavir free base, unless specified otherwise. The pharmaceutical dosage form of the invention is a high per unit dosage of the nelfinavir mesylate as compared to the 250 mg market formulation, and is amenable to oral administration. For patient compliance and acceptability, the maximum weight of a solid unit oral pharmaceutical dosage form is typically from about 1.0 g to about 1.5 g. The present invention encompasses solid unit oral dosage forms having the nelfinavir mesylate in a dose from about 400 mg, the dose at which the gelling potential of the nelfinavir mesylate begins to be problematic when formulated using conventional pharmaceutical excipients and processes, to about 700 mg. Preferably, the dosage form comprises nelfinavir mesylate in an amount of from about 500 mg to about 700 mg. A preferable dosage amount is, for example, 625 mg.

The pharmaceutically acceptable water-soluble, non-ionic synthetic block copolymer of ethylene oxide and propylene oxide in accordance with the present invention has a melting point of at least about 45° C. and a hydrophil/lipophil balance ("HLB") value at 25° C. of from about 18 to about 29.

Pharmaceutically acceptable copolymers of the present invention preferably have a melting point of from about 45° C. to about 57° C., more preferably from about 49° C. to about 57° C. The pharmaceutically acceptable copolymers of the present invention preferably have a HLB value at 25° C. of from about 22 to about 29. The pharmaceutically acceptable copolymers of the present invention preferably have a molecular weight of from about 6,800 D to about 17,500 D.

The copolymer is readily water soluble. Typically, the copolymer of the present invention has a percentage of oxyethylene of from about 70% to about 85%. The copolymer encompasses some of the poloxamers listed in the NF Monograph "Poloxamer". Examples of poloxamers in accordance with the invention include Lutrol® or Pluronic® F68, F87, F108 and F127 (BASF Corporation), which have the following characteristics:

| Lutrol ® | Poloxamer, NF | % Weight Oxyethylene | Molecular Weight (D) | Melting Point (° C.) | HLB Value at 25° C. |
|---|---|---|---|---|---|
| F68 | 188 | 81.8 ± 1.9 | 7680–9510 | 52 | 29 |
| F87 | 237 | 72.4 ± 1.9 | 6840–8830 | 49 | 24 |
| F108 | 338 | 83.1 ± 1.7 | 12700–17400 | 57 | 27 |
| F127 | 407 | 73.2 ± 1.7 | 9840–14600 | 56 | 22 |

The pharmaceutical dosage form of the invention contains the block copolymer in an amount of from about 40% to about 65% by weight of the nelfinavir mesylate, preferably from about 45% to about 60%, and more preferably from about 50% to about 55% by weight of the nelfinavir mesylate.

"Pharmaceutically acceptable", such as in pharmaceutically acceptable excipient, pharmaceutically acceptable non-ionic synthetic block copolymer of ethylene and propylene oxide, etc., means pharmacologically acceptable and substantially non-toxic to the subject to which the referred item is administered. Pharmaceutically acceptable non-ionic synthetic block copolymers of ethylene and propylene oxide of the present invention include, for instance, those having an average molecular weight of from about 6,800 D to about 17,500 D. Pharmaceutically acceptable block copolymers of the present invention are preferably those having a melting point of from about 49° C. to about 57° C.

The nelfinavir mesylate dosage form of the present invention is advantageously produced by a hot melt granulation process. The hot melt granulation process of the present invention comprises blending the nelfinavir mesylate and the copolymer, and heating the blend to a temperature of from the copolymer melting point temperature to below the decomposition temperature of nelfinavir mesylate. The hot melt granulation process results in a melt granulation which comprises granules of the drug embedded in the copolymer. The heated blend is mixed until such melt granules are obtained. Preferably, the blend is heated to a temperature at which the nelfinavir mesylate remains in solid form in the nelfinavir mesylate-copolymer mixture. A jacketed mixer or a hot melt extruder can be used to prepare a melt granulation.

One or more excipients can be included in the mixture of drug and copolymer. The excipient can be selected from the group of stabilizers, wetting agents, binders, disintegrants, diluents and solubilizers. Examples of additives for inclusion in the nelfinavir mesylate-copolymer mixture are povidone, polyethylene glycol, and polyoxyethylene sorbitan esters of $C_8$–$C_{18}$ fatty acids, (e.g., Tween® 20, Tween® 60, and Tween® 80), etc. The heated blend is mixed and melt granules are formed, thus resulting in a melt granulation that includes one or more pharmaceutically acceptable excipients. The melt granulation can then be milled and mixed with one or more pharmaceutical excipients. The excipient added to the milled granulation can be selected from the group of lubricants, disintegrants and diluents. The pharmaceutical excipient may be, for example, microcrystalline cellulose, corn starch, magnesium stearate, etc.

The hot melt granulation process of the present invention comprises hot melt granulating the nelfinavir mesylate in an amount of from about 400 mg to about 700 mg per unit dose with a pharmaceutically acceptable water soluble, non-ionic synthetic block copolymer of ethylene oxide and propylene oxide, the copolymer having a melting point of at least about 45° C., and an HLB value at 25° C. of from about 18 to about 29, wherein the copolymer is present from about 40% to about 65% by weight of the nelfinavir mesylate, at a temperature of from the melting point temperature of the copolymer to below the decomposition temperature of nelfinavir mesylate. Preferably, the temperature is from about 50° C. to about 85° C., with the proviso that the temperature be at least at the melting point temperature of the copolymer. Preferably, the amount of the nelfinavir mesylate used is from about 500 mg to about 700 mg per unit dose, as for example, 625 mg per unit dose. The melt granulation, prepared with or without any additional pharmaceutical excipients, is then processed into a solid unit oral dosage form.

The copolymer of the process of the present invention preferably has an average molecular weight of from about 6,800 D to about 17,500 D, a preferable melting point of from about 45° C. to about 57° C., more preferably from about 49° C. to about 57° C., and a preferable HLB value at 25° C. of from about 22 to about 29.

For preparing tablets, the melt granulation can be processed into a solid unit oral dosage form by milling, lubricating, compressing (tabletting), and, typically, aqueous film coating.

In an embodiment of the present invention, tablets are prepared as follows:

blend amorphous nelfinavir mesylate in an amount of from about 400 mg to about 700 mg (calculated as free base) per unit dosage with the copolymer of the invention in an amount from about 40% to about 65% by weight of the nelfinavir mesylate;

mix the powder blend from step (a) in a jacketed high shear granulator at 60°±10° C. with the proviso that the temperature be at least at the melting point temperature of the copolymer, or in a jacketed hot melt extruder at 80°±5° C., until melt granules are obtained. Cool the melt granulation to room temperature;

mill the granulation from step (b) into a fine powder;

blend the milled granulation from step (c) with other suitable tablet diluents, such as corn starch and microcrystalline cellulose;

lubricate the granulation from step (d) with a suitable lubricant, such as magnesium stearate;

compress the final blend from step (e) on a tablet press;

aqueous film coat the tablet from step (f).

A pharmaceutical dosage form of the invention, can alternatively be prepared by hot melt extrusion, fluid bed process or equipped with or without rotor processor, and jacketed centrifugal granulator or spheronizer.

The solid oral unit dosage form can be a tablet, capsule or caplet. The pharmaceutical composition can include one or more pharmaceutically acceptable excipients selected from the group of stabilizers, wetting agents, binders, disintegrants, diluents, solubilizers and lubricants. For example, the excipient can be microcrystalline cellulose, corn starch, magnesium stearate, povidone, polyethylene glycol, and polyoxyethylene sorbitan esters of $C_8$–$C_{18}$ fatty acids (e.g., Tween® 20, Tween® 60 and Tween® 80), etc.

EXAMPLES

Example I 250 mg Nelfinavir Mesylate Tablet (Market Formulation)

Commercial Viracept® tablets were used in the present Example.

Example II 625 mg Nelfinavir Mesylate Tablet

| Composition | mg/tablet |
| --- | --- |
| Nelfinavir Mesylate | 730.625* |
| Crospovidone | 240.000 |
| Calcium Silicate | 217.375 |
| Purified Water | q.s.** |
| Magnesium Stearate | 12.000 |
| Tablet Weight | 1200.000 |

*Equivalent to 625 mg of Nelfinavir free base
**Removed during processing

The tablet formulation of Example II was produced by a conventional aqueous wet granulation process.

Example III 625 mg Nelfinavir Mesylate Tablet

| Composition | mg/tablet |
| --- | --- |
| Nelfinavir Mesylate | 730.625* |
| Crospovidone | 100.000 |
| Dibasic Calcium Phosphate, Anhydrous | 169.375 |
| Purified Water | q.s.** |
| Magnesium Stearate | 10.000 |
| Tablet Weight | 1010.000 |

*Equivalent to 625 mg of Nelfinavir free base
**Removed during processing

The tablet formulation of Example III was produced by a conventional aqueous wet granulation process.

Example IV 625 mg Nelfinavir Mesylate Tablet of the Invention

| Composition | mg/tablet |
| --- | --- |
| Kernel: | |
| Nelfinavir Mesylate | 730.625* |
| Poloxamer 188 (Lutrol® F68) | 394.375** |
| Corn Starch | 60.000 |
| Magnesium Stearate | 7.000 |
| Kernel Weight | 1192.000 |
| Film Coat: | |
| HPMC 2910-6 cps | 7.341 |
| Pharmacoat 603 | 10.500 |
| Talcum | 5.969 |
| Titanium Dioxide | 5.682 |
| Red Iron Oxide | 0.048 |
| Yellow Iron Oxide | 0.048 |
| Aquacoat ECD-30 | 5.987*** |
| Triacetin | 2.425 |
| Purified Water | 138.030**** |
| Total Weight | 1230.000 |

*Equivalent to 625 mg of Nelfinavir free base
**Approximately 54% w/w of Nelfinavir Mesylate
***Based on dry basis-solids content of a 30% suspension
****Removed during processing; this amount of water does not include the amount of water present in Aquacoat ECD-30

The tablet formulation of Example IV was produced using a hot melt granulation process, as follows:

1. Nelfinavir mesylate and Lutrol® F68 were mixed in a jacketed high shear granulator with a temperature setting at 25°±5° C. for 5 minutes using impeller at low speed and chopper at low speed.

2. The jacketed temperature was raised to 60°±10° C. with the proviso that the temperature was at least at the melting point temperature of the Lutrol® F68, while mixing of the powder blend (step 1) in the high shear granulator was continued using impeller at low speed and chopper at low speed until a suitable granulation was obtained, at which time the impeller and chopper were turned off.

3. The heat to the jacket was turned off. The product was cooled to room temperature by passing tap water (25°±5° C.) into the jacketed vessel, with intermittent jogging of both impeller and chopper at low speed.

4. The granulation from step 3 was passed through a mill.

5. Approximately 50% of the milled granulation from Step 4 was placed into a twin shell blender. Corn starch and magnesium stearate (passed through a #30 mesh stainless steel screen) were added into the blender. The remainder of the milled granulation from step 4 was added to the blender and mixed for 8 minutes.

6. The granulation from step 5 was compressed into a tablet containing nelfinavir mesylate, 625 mg (as free base).

7. The coating suspension was prepared as follows: In a stainless steel container, triacetin and Aquacoat ECD-30 were dispersed in purified water using a propeller mixer, mixing for 45 minutes. HPMC 2910-6 cps, Pharmacoat 603, talcum, titanium dioxide, yellow iron oxide and red iron oxide were added and slowly dispersed, while mixing gently to avoid air entrapment. Mixing was continued for another 60 minutes or until a uniform suspension was obtained.

8. The kernels from step 6 were placed into a perforated coating pan. They were heated with warm inlet air of 50°±3° C. with intermittent jogging until the outlet air temperature reached 38°±3° C.

9. The inlet air temperature was increased to 60°±3° C. The kernels from step 8 were sprayed with the coating suspension from step 7, stirred continuously, using an air spray system and maintaining the outlet air temperature at 38°±3° C. The film coat, 38 mg per tablet, was applied (range 35–41 mg on a dry basis).

10. The inlet air temperature was reduced to 40°±3° C. and the coated tablets were dried by jogging until the loss on drying of the tablets at 90° C. was less than 1.8%. The heat was turned off and the tablets were cooled to room temperature by occasional jogging.

Example V 625 mg Nelfinavir Mesylate Tablet of the Invention

| Composition | mg/tablet |
| --- | --- |
| Kernal: | |
| Nelfinavir Mesylate | 730.625* |
| Poloxamer 188 (Lutrol ® F68) | 394.375** |
| Microcrystalline Cellulose | 40.000 |
| Corn Starch | 20.000 |
| Magnesium Stearate | 7.000 |
| Kernel Weight | 1192.000 |
| Film Coat: | |
| HPMC 2910-6 cps | 13.140 |
| Talcum | 4.085 |
| Titanium Dioxide | 4.084 |
| FD&C Blue #2 | 0.591 |
| Aquacoat ECD-30 | 4.400*** |
| Triacetin | 1.700 |
| Purified Water | 117.290**** |
| Total Weight | 1220.000 |

*Equivalent to 625 mg of Nelfinavir free base
**Approximately 54% w/w of Nelfinavir Mesylate
***Based on dry basis-solids content of a 30% suspension
****Removed during processing; this amount of water does not include the amount of water present in Aquacoat ECD-30

The melt granulation method set forth in Example IV was used with the composition amounts set forth in the table above for the present example. Differences in the tablet coating are reflected in the following steps numbered 7 and 9 that here replace steps 7 and 9 of Example IV.

7. The coating suspension was prepared as follows: In a stainless steel container, triacetin and Aquacoat ECD-30 were dispersed in purified water using a propeller mixer, mixing for 45 minutes. HPMC 2910-6 cps, talcum, titanium dioxide and FD&C Blue #2 were added and slowly dispersed, while mixing gently to avoid air entrapment. Mixing was continued for another 60 minutes or until a uniform suspension was obtained.

9. The inlet air temperature was increased to 60°±3° C. The kernels from step 8 were sprayed with the coating suspension from step 7, then stirred continuously, using an air spray system and maintaining the outlet air temperature at 38°±3° C. The film coat, 28 mg per tablet, was applied (range 25–31 mg on a dry basis).

Example VI 625 mg Nelfinavir Mesylate Tablet

| Composition | mg/tablet |
| --- | --- |
| Nelfinavir Mesylate | 730.625* |
| Poloxamer 188 (Lutrol ® F68) | 182.656** |
| Corn Starch | 102.616 |
| Magnesium Stearate | 10.262 |
| Tablet Weight | 1026.159 |

*Equivalent to 625 mg of Nelfinavir free base
**Approximately 25% w/w of Nelfinavir Mesylate The tablet formulation of Example VI was produced by hot melt granulation, as follows:

Nelfinavir mesylate and Lutrol® F68 were blended in a mixer for 10 minutes.

The powder mixture from step 1 was added to a jacketed hot melt extruder set at 80°±+5° C. while thorough mixing was continued until a uniform melt mixture was obtained.

Steps 3 to 6 under Example IV were then followed as steps 3 to 6 of the present example.

Example VII 625 mg Nelfinavir Mesylate Tablet

| Composition | mg/tablet |
| --- | --- |
| Nelfinavir Mesylate | 730.625* |
| Poloxamer 188 (Lutrol ® F68) | 243.542** |
| Corn Starch | 109.457 |
| Magnesium Stearate | 10.946 |
| Tablet Weight | 1094.570 |

*Equivalent to 625 mg of Nelfinavir free base
**Approximately 33% w/w of Nelfinavir Mesylate The same hot melt granulation procedure was followed as described in Example VI.

Example VIII 625 mg Nelfinavir Mesylate Tablet of the Invention

| Composition | mg/tablet |
| --- | --- |
| Nelfinavir Mesylate | 730.625* |
| Poloxamer 188 (Lutrol ® F68) | 343.824** |
| Corn Starch | 120.725 |

-continued

| Composition | mg/tablet |
| --- | --- |
| Magnesium Stearate | 12.073 |
| Tablet Weight | 1207.247 |

*Equivalent to 625 mg of Nelfinavir free base
**Approximately 47% w/w of Nelfinavir Mesylate The same hot melt granulation procedure was followed as described in Example VI.

Example IX 625 mg Nelfinavir Mesylate Tablet of the Invention

| Composition | mg/tablet |
| --- | --- |
| Nelfinavir Mesylate | 730.625* |
| Poloxamer 188 (Lutrol ® F68) | 443.215** |
| Corn Starch | 131.892 |
| Magnesium Stearate | 13.189 |
| Tablet Weight | 1318.921 |

*Equivalent to 625 mg of Nelfinavir free base
**Approximately 61% w/w of Nelfinavir Mesylate The same hot melt granulation procedure was followed as described in Example VI.

Example X

Dissolution Testing

Tablet formulations containing nelfinavir mesylate (Examples I–IX) were evaluated for dissolution in 900 mL of 0.1N hydrochloric acid solution equilibrated at 37°±0.5° C. using a paddle method (USP Apparatus 2) at 50 rpm. Sample aliquots were taken at different time intervals and analyzed by UV spectrophotometry.

FIG. 1 presents dissolution profiles of 625 mg tablet formulations of nelfinavir mesylate which do not contain the block copolymer of the present invention (Examples II and III) compared to that of the 250 mg market (tablet) formulation (Example I). The dissolution profiles of 625 mg nelfinavir mesylate tablets without block copolymer (Examples II and III) were significantly slower and less complete than that of the 250 mg market (tablet) formulation (Example I). The tablet formulations of Examples II and III contain conventional excipients and were produced by a conventional aqueous wet granulation process.

Figure 2:
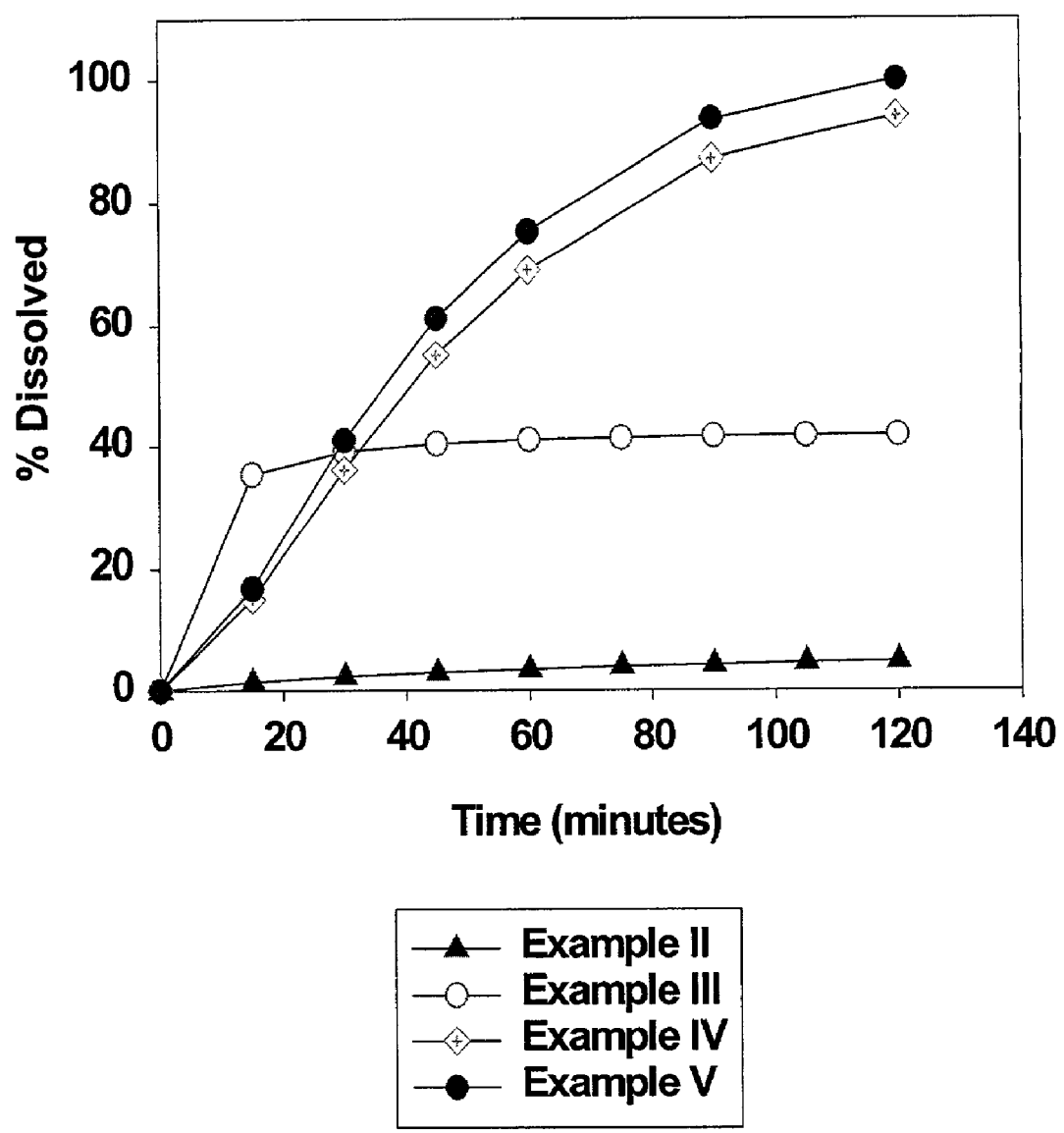
FIG. 2 presents dissolution profiles of 625 mg nelfinavir mesylate tablets in accordance with the invention (Examples IV and V) compared to other 625 mg nelfinavir mesylate tablets (Examples II and III).

As shown in FIG. 2, the results of the dissolution evaluation indicate that the dissolution profiles of 625 mg nelfinavir mesylate tablets in accordance with the invention (Examples IV and V) were significantly faster and essentially complete compared to the dissolution profiles of the 625 mg nelfinavir mesylate tablets which were prepared using conventional pharmaceutical excipients and a conventional aqueous wet granulation process (Examples II and III).

Figure 3:
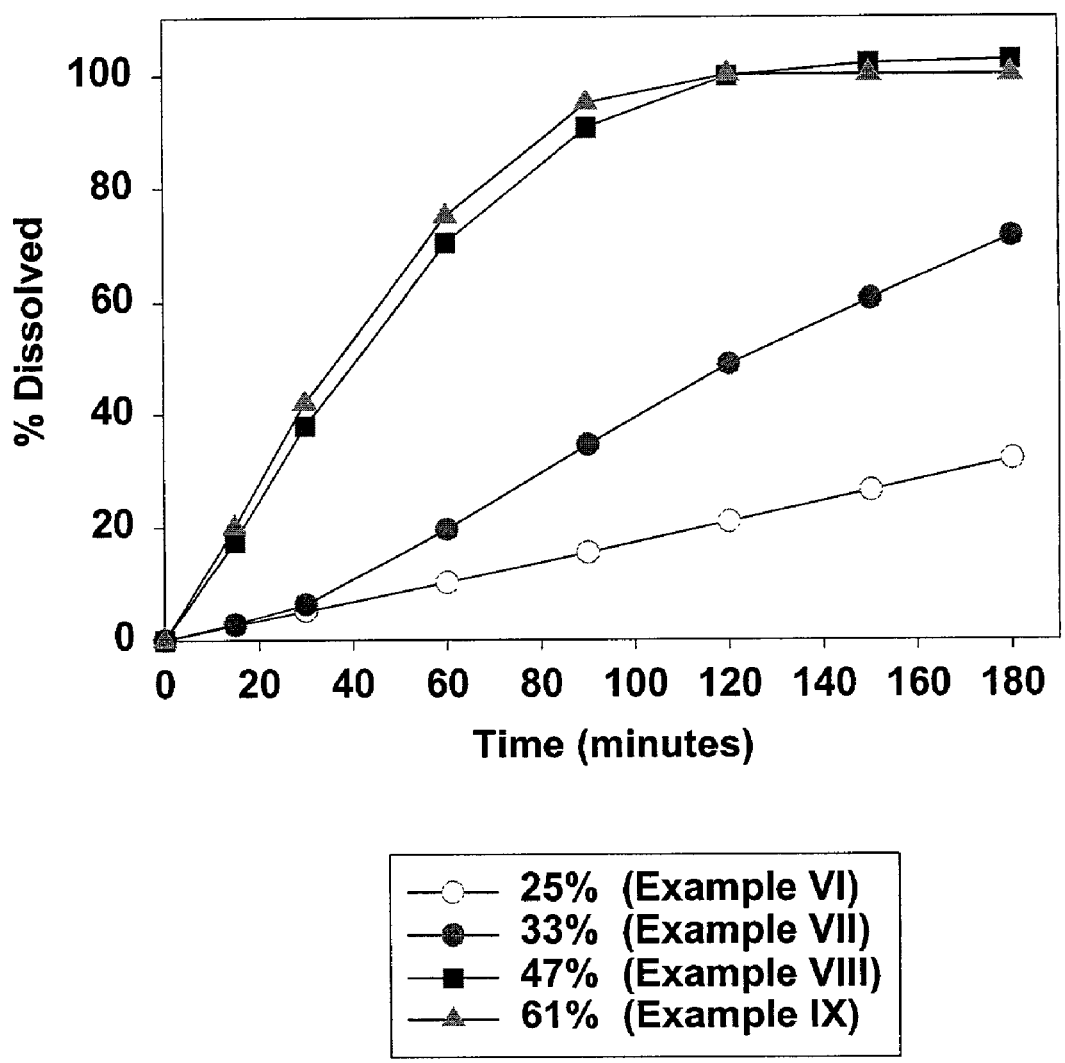
FIG. 3 shows the effect of Poloxamer 188 concentration on the dissolution profiles of 625 mg tablets of nelfinavir mesylate (Examples VI, VII, VIII and IX).

The dissolution profiles of tablets of Examples VI through IX are shown in FIG. 3. The results indicate that the concentration of block copolymer plays a significant role with respect to the rate and completeness of dissolution of nelfinavir mesylate. Examples VI and VII contain Poloxamer 188 in an amount of 25% and 33% by weight of nelfinavir mesylate, respectively. Examples VIII and IX, which contain Poloxamer 188 in an amount of 47%, and 61% by weight of nelfinavir mesylate, respectively, are within the scope of the invention. The dissolution profiles of Examples VIII and IX show faster and more complete release.

Example XI

Pharmacokinetic Testing

Nelfinavir mesylate 250 mg tablets of the market formulation (Example I) and nelfinavir mesylate 625 mg tablets of the invention (Example IV) were evaluated for bioavailability in man. Each subject was administered a number of tablets of the given formulation totaling 1250 mg of nelfinavir mesylate (calculated as free base). In this study, 13 blood samples were drawn for each pharmacokinetic profile, i.e. at pre-dose, and at 1, 2, 3, 4, 5, 6, 8, 10, 12, 15, 18, and 24 hours after administration of the drug. Venous blood samples of approximately 5 mL were collected into heparinized tubes. Plasma was separated by centrifugation at 1500 g and 4° C. for 10 minutes, within 60 minutes of drawing the blood. Plasma samples were subsequently stored at −20° C. until analysis. Nelfinavir content in the plasma samples was determined by liquid chromatography—tandem mass spectrometry (LC-MS/MS). The limit of quantification was set to 4 ng/mL.

The plasma concentration versus time profiles were used for the estimation of pharmacokinetic parameters. Standard non-compartmental methods were applied using the software WinNonlin 3.1. The pre-dose sampling time of a profile was set to zero and the post-dose sampling times were used as actual times. The following parameters were estimated:

$C_{max}$, maximum observed plasma concentration $t_{max}$, time of maximum observed plasma concentration $AUC_{0-24}h$, calculated using WinNonlin computational rules for partial AUCs and the linear trapezoidal rule $AUC_{0-inf}$, calculated by $AUC_{last}+(C_{last})/k$, where an assessment of k (terminal elimination rate constant) was feasible $t_{1/2}$, terminal half-life, calculated by $Ln(2)/k$, where an assessment of k was feasible The results of this bioavailability evaluation are given in Table I below.

TABLE I

Summary of pharmacokinetic parameters after administration of 1250 mg of nelfinavir mesylate (as free base)*: 2 × 625 mg tablets of the invention (Example IV) compared to 5 × 250 mg tablets of the market formulation (Example I)

| | Nelfinavir 1250 mg (based on the free base) | |
| --- | --- | --- |
| Parameter (Unit) | Example I N = 12 | Example IV N = 12 |
| $AUC_{0-24}$ (× 10³ hr ng/mL) | | |
| Median (Min–Max) | 43.5 (21.1–89.7) | 37.0 (27.5–73.2) |
| Mean | 44.4 | 42.3 |
| Geometric Mean | 41.8 | 40.0 |
| CV % | 38.6 | 37.4 |
| $C_{max}$ (ng/mL) | | |
| Median (Min–Max) | 5275 (2520–9590) | 4585 (3680–8450) |
| Mean | 5248 | 5200 |

TABLE I-continued

Summary of pharmacokinetic parameters after administration of 1250 mg of nelfinavir mesylate (as free base)*: 2 × 625 mg tablets of the invention (Example IV) compared to 5 × 250 mg tablets of the market formulation (Example I)

| | Nelfinavir 1250 mg (based on the free base) | |
|---|---|---|
| Parameter (Unit) | Example I<br>N = 12 | Example IV<br>N = 12 |
| Geometric Mean | 4971 | 5042 |
| CV % | 34.9 | 27.7 |
| $t_{max}$ (hr) | | |
| Median (Min–Max) | 4.0 (3.0–6.0) | 4.0 (2.0–6.0) |
| Mean | 4.1 | 4.0 |
| CV % | 26.5% | 35.4% |
| $AUC_{0-inf}$ (× $10^3$ hr ng/mL) | | |
| Median (Min–Max) | 45.3 (21.7–98.2) | 37.8 (28.5–77.7) |
| Mean | 46.5 | 43.7 |
| Geometric Mean | 43.5 | 41.1 |
| CV % | 41.2% | 39.7% |
| $t_{1/2}$ (hr) | | |
| Median (Min–Max) | 4.4 (3.3–6.8) | 3.9 (3.0–5.7) |
| Mean | 4.5 | 3.9 |
| Harmonic Mean | 4.3 | 3.8 |
| CV % | 24.9% | 22.0% |

*With food

Figure 4:
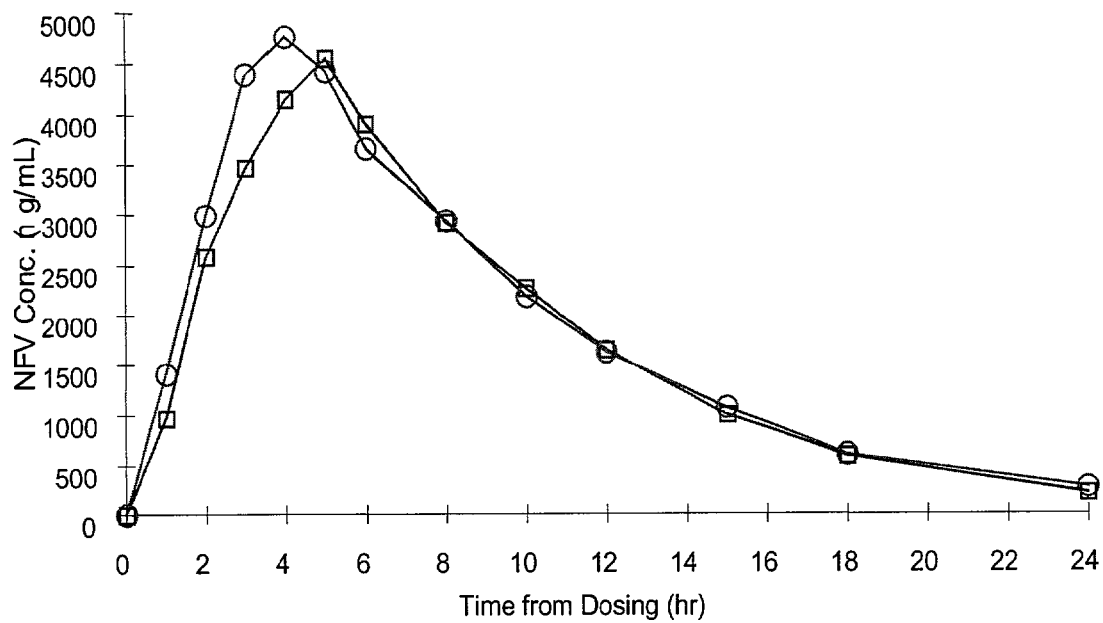
FIG. 4 shows mean plasma concentration versus time profiles after administration of 2×625 mg nelfinavir mesylate tablets of the invention (Example IV) compared to administration of 5×250 mg tablets of the market formulation (Example I).

The data reported in Table I and plotted in FIG. 4 indicate that the bioavailability in man of 2×625 mg nelfinavir mesylate tablets of the invention (Example IV) was comparable to that of 5×250 mg tablets of the market formulation (Example I) when administered with food. The present invention advantageously provides high dosage solid unit oral pharmaceutical compositions of nelfinavir mesylate having satisfactory dissolution and bioavailability.

What is claimed is:

1. A solid unit oral pharmaceutical dosage form of amorphous nelfinavir mesylate comprising amorphous nelfinavir mesylate in an amount of from about 400 mg to about 700 mg calculated as nelfinavir base, and a pharmaceutically acceptable water soluble, non-ionic synthetic block copolymer of ethylene oxide and propylene oxide, said copolymer having a melting point of at least about 45° C. and an HLB value at 25° C. of from about 18 to about 29, wherein said copolymer is present from about 40% to about 65% by weight of the nelfinavir mesylate.

2. The dosage form according to claim 1, which is selected from the group consisting of a tablet, a capsule and a caplet.

3. The dosage form according to claim 2, which is a tablet.

4. The dosage form according to claim 1, wherein said copolymer is present from about 45% to about 60% by weight of the nelfinavir mesylate.

5. The dosage form according to claim 4, wherein said copolymer is present from about 50% to about 55% by weight of the nelfinavir mesylate.

6. The dosage form according to claim 1, wherein said copolymer is selected from the group consisting of Poloxamer 188, Poloxamer 237, Poloxamer 338 and Poloxamer 407.

7. The dosage form according to claim 1, wherein said copolymer is Poloxamer 188.

8. The dosage form according to claim 1, wherein said nelfinavir mesylate is in an amount of from about 500 mg to about 700 mg calculated as nelfinavir base.

9. The dosage form according to claim 8, wherein said nelfinavir mesylate is in an amount of about 625 mg calculated as nelfinavir base.

10. The dosage form according to claim 1, having a weight of from about 1.0 g to about 1.5 g.

11. The dosage form according to claim 1, wherein said copolymer has a HLB value at 25° C. from about 22 to about 29.

12. The dosage form according to claim 1, wherein said copolymer has an average molecular weight of from about 6,800 D to about 17,500 D.

13. The dosage form according to claim 1, wherein said copolymer has a melting point of at least about 49° C.

14. The dosage form according to claim 13, wherein said copolymer has a melting point of from about 49° C. to about 57° C.

15. The dosage form according to claim 1, further comprising a pharmaceutically acceptable excipient selected from the group consisting of stabilizers, wetting agents, binders, disintegrants, diluents, solubilizers, and lubricants.

16. The dosage form according to claim 1, further comprising a pharmaceutically acceptable excipient selected from the group consisting of microcrystalline cellulose, corn starch, magnesium stearate, polyethylene glycol, polyoxyethylene sorbitan esters of $C_8$–$C_{18}$ fatty acids, and povidone.

17. A process for making a solid unit oral pharmaceutical dosage form of amorphous nelfinavir mesylate, comprising the steps of:
   (a) heating a blend comprising amorphous nelfinavir mesylate in an amount of from about 400 mg to about 700 mg calculated as nelfinavir base per unit dosage and a pharmaceutically acceptable water soluble, nonionic synthetic block copolymer of ethylene oxide and propylene oxide, said copolymer having a melting point of at least about 45° C. and an HLB value at 25° C. of from about 18 to about 29, in an amount of said copolymer that is from about 40% to about 65% by weight of said nelfinavir mesylate, at a temperature of from the melting point temperature of the copolymer to below the decomposition temperature of nelfinavir mesylate,
   (b) mixing the blend to form a melt granulation, and
   (c) processing the melt granulation into said dosage form of amorphous nelfinavir mesylate.

18. The process according to claim 17, wherein step (c) comprises milling the melt granulation, adding a pharmaceutically acceptable excipient and compressing.

19. The process according to claim 18, wherein said pharmaceutically acceptable excipient is selected from the group consisting of lubricants, disintegrants and diluents.

20. The process according to claim 18, wherein said pharmaceutically acceptable excipient is selected from the group consisting of microcrystalline cellulose, corn starch and magnesium stearate.

21. The process according to claim 17, wherein said blend of step (a) further comprises a pharmaceutically acceptable excipient.

22. The process according to claim 21, wherein said pharmaceutically acceptable excipient is selected from the group consisting of stabilizers, wetting agents, binders, disintegrants, diluents, and solubilizers.

23. The process according to claim 21, wherein said pharmaceutically acceptable excipient is selected from the group consisting of polyethylene glycol, polyoxyethylene sorbitan esters of $C_8$–$C_{18}$ fatty acids, and povidone.

24. The process according to claim 17, wherein said heating of step (a) is at a temperature of from about 50° C.

to about 85° C., with the proviso that the temperature be at least at the melting point temperature of the copolymer.

25. The process according to claim 17, wherein said copolymer has an average molecular weight of from about 6,800 D to about 17,500 D, a melting point of from about 49° C. to about 57° C. and an HLB value at 25° C. of from about 22 to about 29.

26. A solid unit oral pharmaceutical dosage form of amorphous nelfinavir mesylate comprising amorphous nelfinavir mesylate in an amount of from about 400 mg to about 700 mg calculated as nelfinavir base, and a water soluble, non-ionic synthetic block copolymer of ethylene oxide and propylene oxide, said copolymer having an average molecular weight of from about 6,800 D to about 17,500 D, a melting point of from about 49° C. to about 57° C. and an HLB value at 25° C. of from about 22 to about 29, wherein said copolymer is present from about 40% to about 65% by weight of the nelfinavir mesylate.

27. The dosage form according to claim 26, wherein said copolymer is present from about 45% to about 60% by weight of the nelfinavir mesylate.

28. The dosage form according to claim 27, wherein said copolymer is present from about 50% to about 55% by weight of the nelfinavir mesylate.

29. The dosage form according to claim 26, wherein said nelfinavir mesylate is in an amount of from about 500 mg to about 700 mg calculated as nelfinavir base.

* * * * *